United States Patent [19]

Knopf et al.

[11] Patent Number: 5,061,630

[45] Date of Patent: Oct. 29, 1991

[54] LABORATORY APPARATUS FOR OPTIONAL TEMPERATURE-CONTROLLED HEATING AND COOLING

[75] Inventors: Ulrich C. Knopf, Freiburg; Joseph Sieber, Zurich, both of Switzerland

[73] Assignee: Agrogen Foundation, Seyffer & Co. & Ulrich C. Knopf, Switzerland

[21] Appl. No.: 350,803

[22] Filed: May 12, 1989

[30] Foreign Application Priority Data

May 13, 1988 [CH] Switzerland ........................ 01918/88
Apr. 21, 1989 [CH] Switzerland ........................ 01519/89

[51] Int. Cl.[5] ................................................ C12M 1/38
[52] U.S. Cl. ....................................... 435/290; 62/3.3; 62/3.62
[58] Field of Search ...................... 62/3.3, 3.62, 457.9; 435/290, 287

[56] References Cited

U.S. PATENT DOCUMENTS

| | | | |
|---|---|---|---|
| 3,552,133 | 1/1971 | Lukomsky | 62/3.3 |
| 4,364,234 | 12/1982 | Reed | 62/3.3 |
| 4,384,512 | 5/1983 | Keith | 62/3.3 |
| 4,402,185 | 9/1983 | Perchak | 62/3.3 |
| 4,453,385 | 6/1984 | May | 62/3.62 |
| 4,823,554 | 4/1989 | Trachtenberg et al. | 62/3.3 |

*Primary Examiner*—Carroll B. Dority
*Attorney, Agent, or Firm*—Frank P. Presta

[57] ABSTRACT

Laboratory apparatus for optionally heating or cooling samples, comprising a block of one or more Peltier elements which, with one of their thermal poles, are in thermal contact with an essentially rectangular block of heat conducting metal, and with the other pole are in thermal contact with a heat exchanger, this latter being thermally insulated from the metal block. One of the outer surfaces of the rectangular metal block serves as a working outer surface for heating or cooling the samples. All outer surfaces of the metal block, with the excption of the working surface and the surface in contact with the Peltier elements, are thermally insulated. The working surface may be used for heating or cooling at will through the inversion of the direction of the alimentation current for the Peltier elements.

19 Claims, 8 Drawing Sheets

LABORATORY APPARATUS FOR OPTIONAL TEMPERATURE-CONTROLLED HEATING AND COOLING

BACKGROUND AND SUMMARY OF THE INVENTION

In biochemical, biological or genetic laboratories the problem of bringing small quantities of a material to a defined temperature and to keep it at this temperature during a certain time is encountered very often. Devices for this task are well known and are offered commercially. Liquid baths, especially water baths controlled by thermostats are well known devices. They generally consist of a vessel, mostly containing a volume of several litres, which is equipped with an electric heating device, a stirrer and sometimes with a circulating pump. The heating device can be controlled by a thermostat in such a manner that the temperature of the circulated liquid is hold at a predetermined temperature. In some cases a cooling device for the liquid bath, by which the temperature of the liquid can be brought to temperatures below ambient temperature, is offered as well. Such a liquid bath can also be used as a cryostat. In general, the cooling device for such cryostats consists of a conventional cooling machine, working by compression or absorption of a cooling medium.

Liquid baths, which, by heating or cooling can be hold at constant temperature are useful and practical to handle for many laboratory tasks. They are suited both for the handling of samples in vessels, which can be put directly into the liquid bath and also for heating or cooling samples through externally circulating the heat transporting liquid.

For heating samples of different volume, especially for liquid samples there also exist electric heating plates, which in some cases may be equipped with a temperature sensor and a thermostat. Heating plates additionally equipped with a rotating permanent magnet are known as well. By putting a magnetic rod into the sample, this latter can be stirred while being heated or cooled.

However a disadvantage of all laboratory thermostats with a liquid bath as described above is their heavy weight and great volume. Compared with the volume of the samples to be heated or cooled, their need for energy is rather high as well. The heating plates commercially available, with or without a stirring device, by their nature are only suited where the temperature of the sample is to be hold above room temperature.

For the biochemical, biological or genetic laboratory, for instance for work with living cells or cell components such as protoplasts or cell nuclei or with living tissues, embryos and organs, cycles are sometimes demanded, whose temperatures are situated partly below and partly above room temperature. Compared to practice in the chemical or physical laboratories the temperatures to be attained in general are not very much above or below room temperature. The typical range in the biological or biochemical laboratory may be between −5° and +60° C.

The conditions of the biological laboratory imply some special requirements in other respects as well: Some kinds of vessels which are used very often, such as the flat Petri disks, are not well suited for the use in a liquid bath; the alcohol, which is very often used as a cooling medium in liquid baths, is undesired in biological laboratories because of the activity of its vapour; restricted space, which is the rule in laminar air flow cabinets, calls for small apparatus. Maintaining sterility is very often an important requirement as well.

Water ice, which in the biological laboratory is used very often, has many disadvantages: It has to be constantly renewed and for its preparation needs a machine which is relatively expensive and spacious. Ice is difficult to be kept sterile; its handling, e.g. for Petri disks is sometimes not very practical. Its constant temperature of 0° C. is a further disadvantage. Lower temperatures may be attained by adding salt, but the programming of temperature cycles remains difficult in this case as well.

It is the scope of this invention to create a laboratory apparatus especially suited to fulfill the needs of the biological, biochemical or genetic laboratory. It is easily manageable for heating or cooling samples of liquids or of biological material and for leading them through determined temperature cycles and its asks for only little room and energy. It is especially conceived to accomplish cycles with temperatures lying partially above and partially below room temperature. It is easy to sterilize and to be kept sterile. It can be equipped with the necessary devices to stir the samples, or, thanks to its small volume and weight, can even be installed on a conventional shaking machine. The separation into a working unit on the one side and a control unit on the other side is of special advantage for such cases.

BRIEF DESCRIPTION OF THE DRAWINGS

The disposition of the apparatus is illustrated by the following FIGS. 1 to 8, without however restricting by them the possible forms of the invention.

DESCRIPTION OF THE PREFERRED EMBODIMENTS

Figure 2:
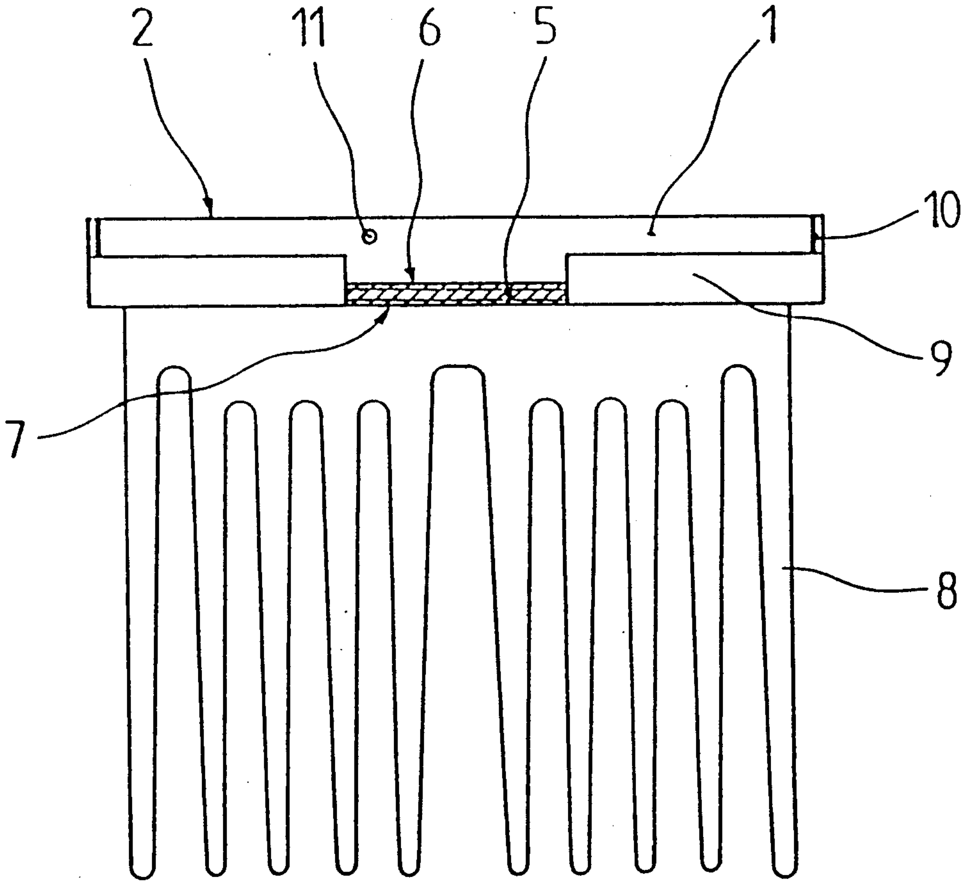
FIG. 2 is an elevations view in section of the apparatus with the metal block (1), its working surface (2), one Peltier element (5) with its upper (6) and lower (7) thermal pole surfaces, the internal temperature sensor (11) incorporated in the metal block, the ribbed heat exchanger (8) and the insulating layers (9) and (10).
Figure 4A:
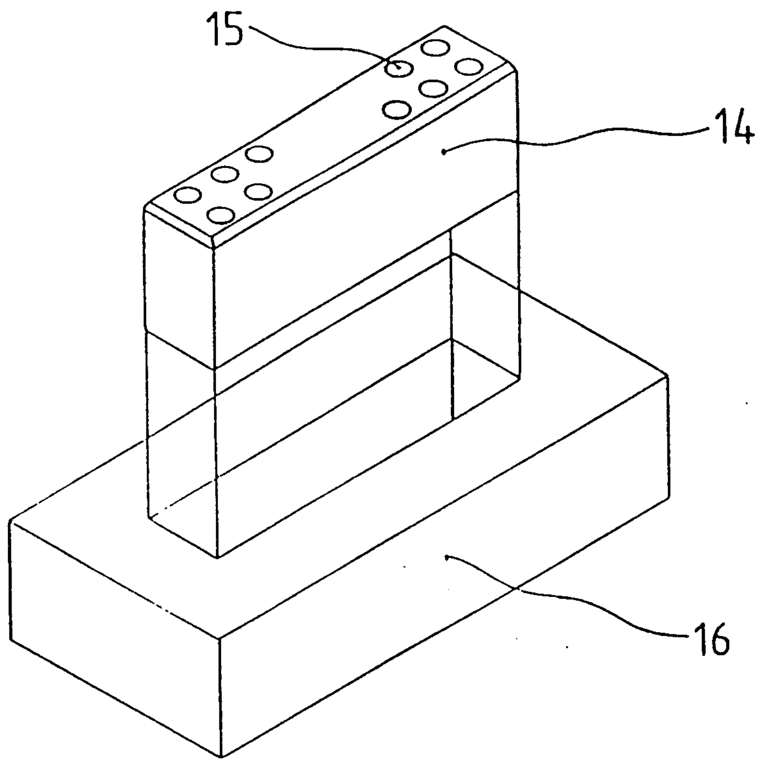
FIGS. 4*a* and 4*b* are perspective views showing the apparatus with a working module in the form of a metal block (14) with openings (15) in which to receive the sample vessels. The insulation envelope (16), which, if occasion arrives, may be removable, is protecting the module from heat exchange with the environment.
Figure 4B:
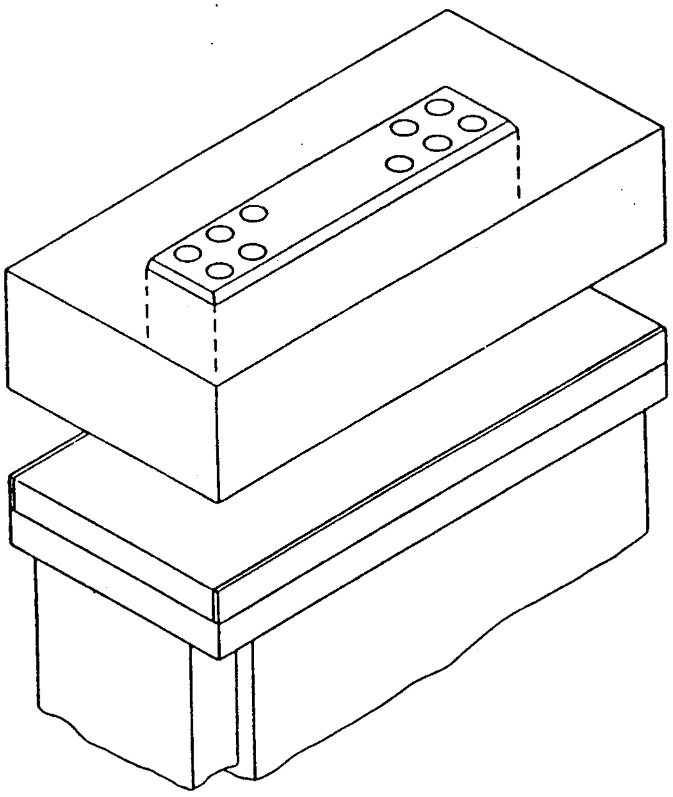
Figure 7:
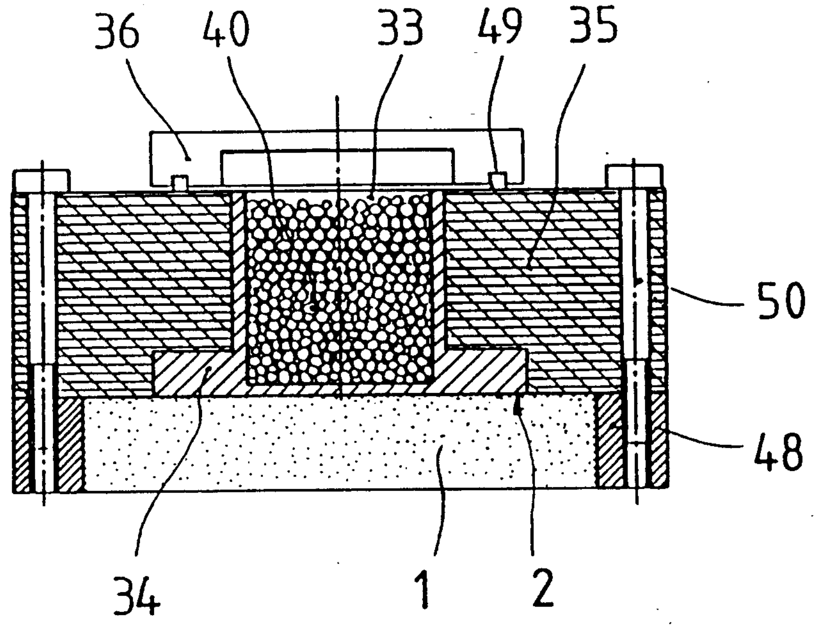
FIG. 7 is a cross section through the module shown in FIG. 6 along the line A—A, whereby the open trough (33) is filled with spheres (40). The working surface (1) of the metal block (2) is shown with a part of its insulation layer (48); the screws (50) are used to fix the module on the metal block (1) of the heating and cooling unit.

The working part of the apparatus as shown in the drawing, FIG. 2, comprise a block (1) of heat conducting metal, preferably aluminum or stainless steel, which can be heated or cooled electrically, with a flat working surface (2) onto which a vessel containing the sample, or—in a different form of the invention—a working module (14, 17, 33) as shown in FIGS. 4, 5 and 7, with one or preferably several openings for the sample vessels.

Figure 1:
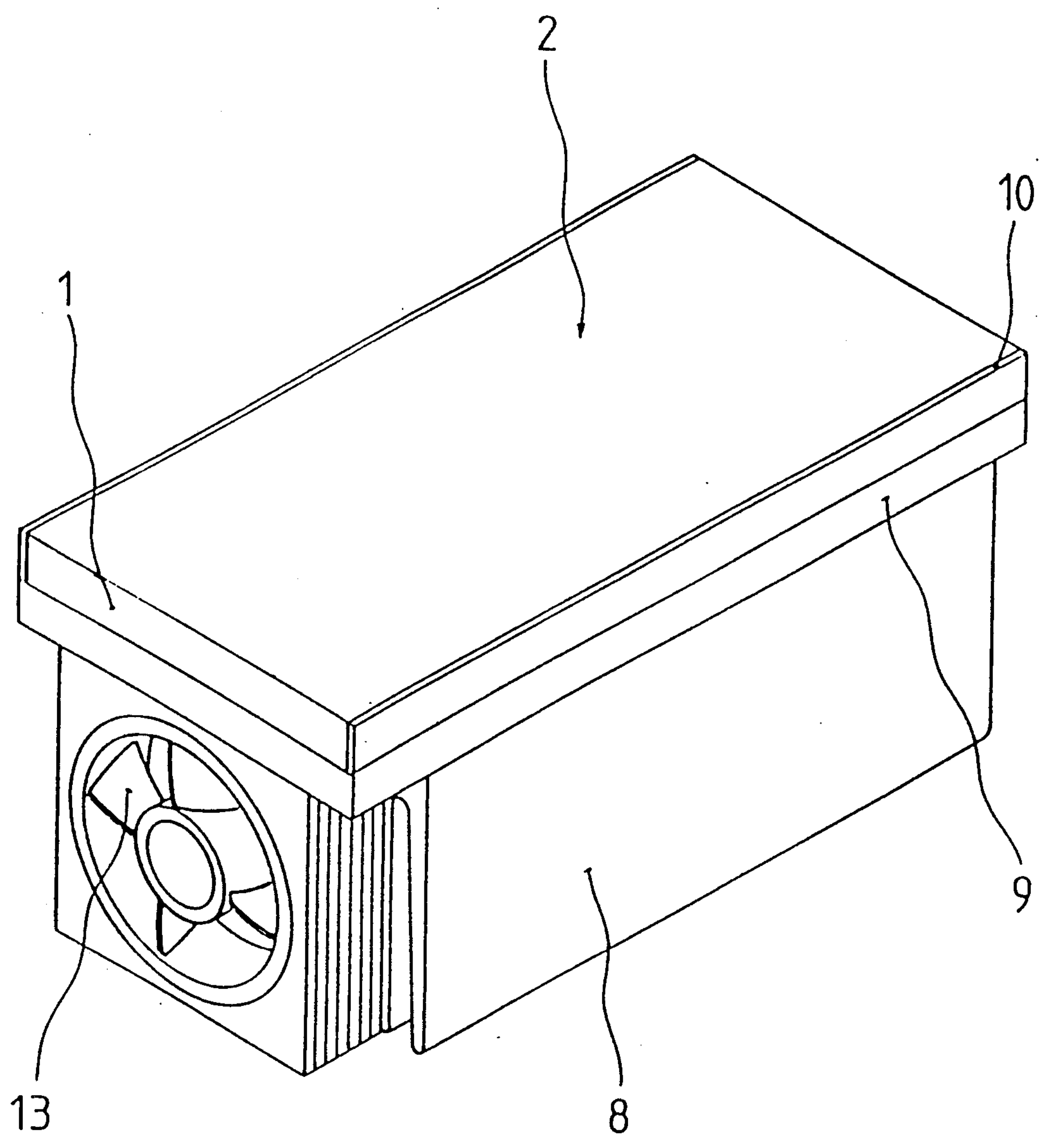
FIG. 1 is a perspective view of the apparatus according to the invention, with the metal block (1) to be heated or cooled, the working surface (2), two Peltier elements (5), a stirring device (12), the heat exchanger (8) with ribs, the ventilator (13) and the insulating layers (9) and (10).

In the metal block (1) of the working part there are placed, near its center, one or several Peltier elements (5) whose surfaces (6) and (7), which are the thermally active poles, are in contact with the metal block (1) on the one side and with the heat exchanger (8) on the other side. The latter is separated from the metal block (1) by an insulating layer (9). A further insulating layer (10, 48) is surrounding the metal block (1). A stirring device (12) may be placed in the center of the metal block (1) near or in between the Peltier elements (5), as shown in FIG. 1.

The Peltier elements (5) possess the shape of rectangular blocks formed by a great number of semiconductor pairs in a parallel arrangement and electrically connected in series. When sending a direct current through it, one of the surfaces of the Peltier element is heated, whereas the opposite surface is cooled correspondingly. By inversion of the direction of the current the heated and cooled surfaces can be interchanged at will. In the following the two surfaces which are heated or cooled respectively are called the thermal pole surfaces of the Peltier block.

For using with the apparatus in the heating mode the direction of electric current is chosen in such a manner, that the upper thermal pole surface (6) is heated and the opposite surface (7) is cooled. The heat thus generated is transferred to the metal block (1), on whose upper surface (2) the samples or the working module containing the sample vessels to be heated are placed; the cold generated at the lower surface (7) is transferred to the heat exchanger (8).

To enhance the heating or cooling effect the number of Peltier elements can be increased as the occasion demands. If several Peltier elements, e.g. arranged in a single layer, are connected electrically in parallel, the total thermal effect is multiplied corresponding to the number of the elements used. In such an arrangement the temperature difference between the pole surfaces of the Peltier elements remains essentially constant and depends from the thermal conductivity inside the Peltier elements alone. However it is possible to arrange the Peltier elements in a stack of two or more layers superimposed vertically onto one another. In such an arrangement every two adjacent elements have to be in contact by their opposite pole surfaces, whereas the elements are electrically connected in series. In such a stack the thermal arrangement of the elements is in series; the temperature difference between the pole surfaces at the ends of the stack, which are in contact with the metal block (1) on the one side and with the heat exchanger (8) on the other side, can thus be increased. It is obvious, when using a greater number of Peltier elements, to connect them partly in parallel and partly in series.

Figure 3:
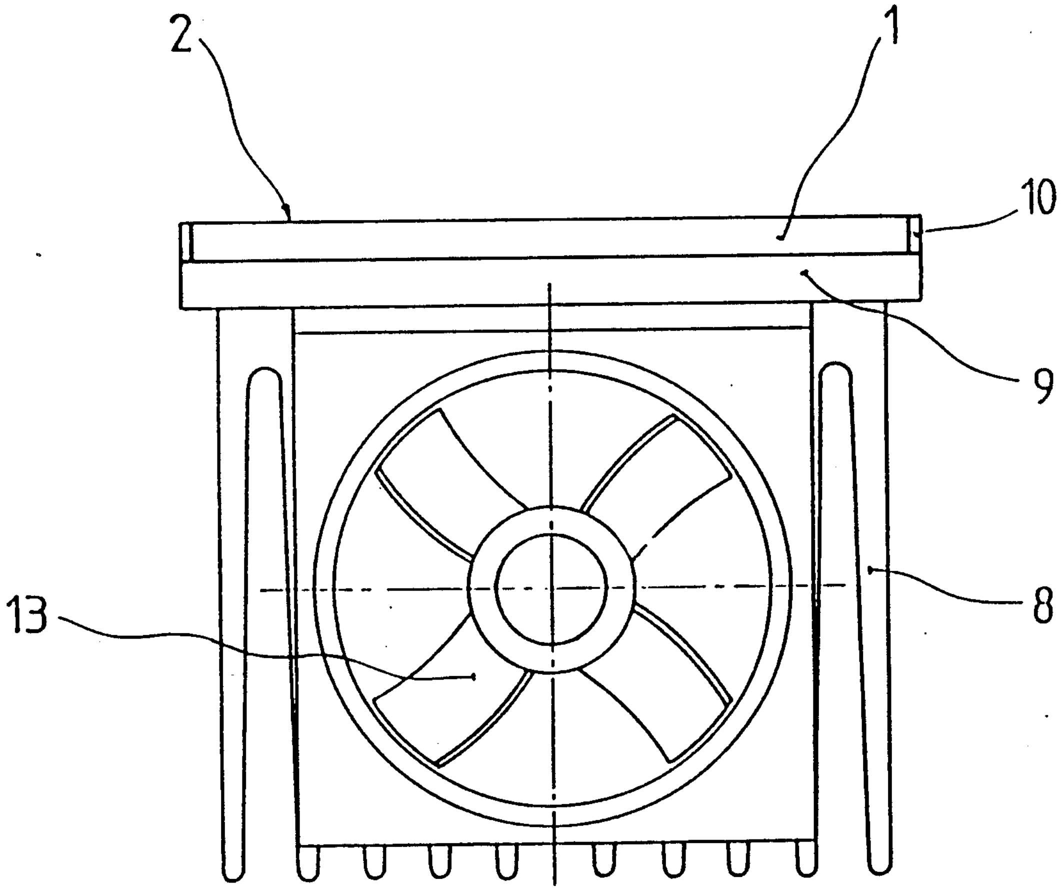
FIG. 3 is a front elevational view of the apparatus towards the ventilator (13).

In one form of the invention, the heat exchanger consists of a metal block with a system of channels in its interior, through which a cooling medium, e.g. water can be circulated. In another form, which is illustrated by the FIGS. 1 to 3, the heat exchanger consists of a metal block whose outer surface is enlarged in the form of ribs. By blowing a stream of air onto the ribs by means of a ventilator (13) the heat exchange can be enhanced. The temperature difference between the pole surfaces of the Peltier elements can thus be minimized and the efficiency of the apparatus be optimized.

To switch the operation of the cooling mode, the direction of the electric current through the Peltier elements is inversed, whereby the upper surface (6) of the Peltier block is cooled, and the lower surface (7) is heated. The metal block (1) is thus cooled; the heat generated at the lower surface (7) is transferred to the heat exchanger (8) and carried away to the environment.

The working part of the apparatus with its metal block (1) for heating and cooling the samples is supplemented by additional exchangeable working modules. The latter can be provided with openings for whole series of sample vessels, such as test tubes, ampoules, or thin tubes, known as "straws". Such block-shaped modules selected for different kinds of sample vessels can simply be put onto the working surface of the metal block (1) or, if needed, are fixed thereon by screws. Of course the contacting faces must be exactly machined in order to ensure good heat transition. All non-contacting outer surfaces of the modules are thermally insulated.

Figure 6:
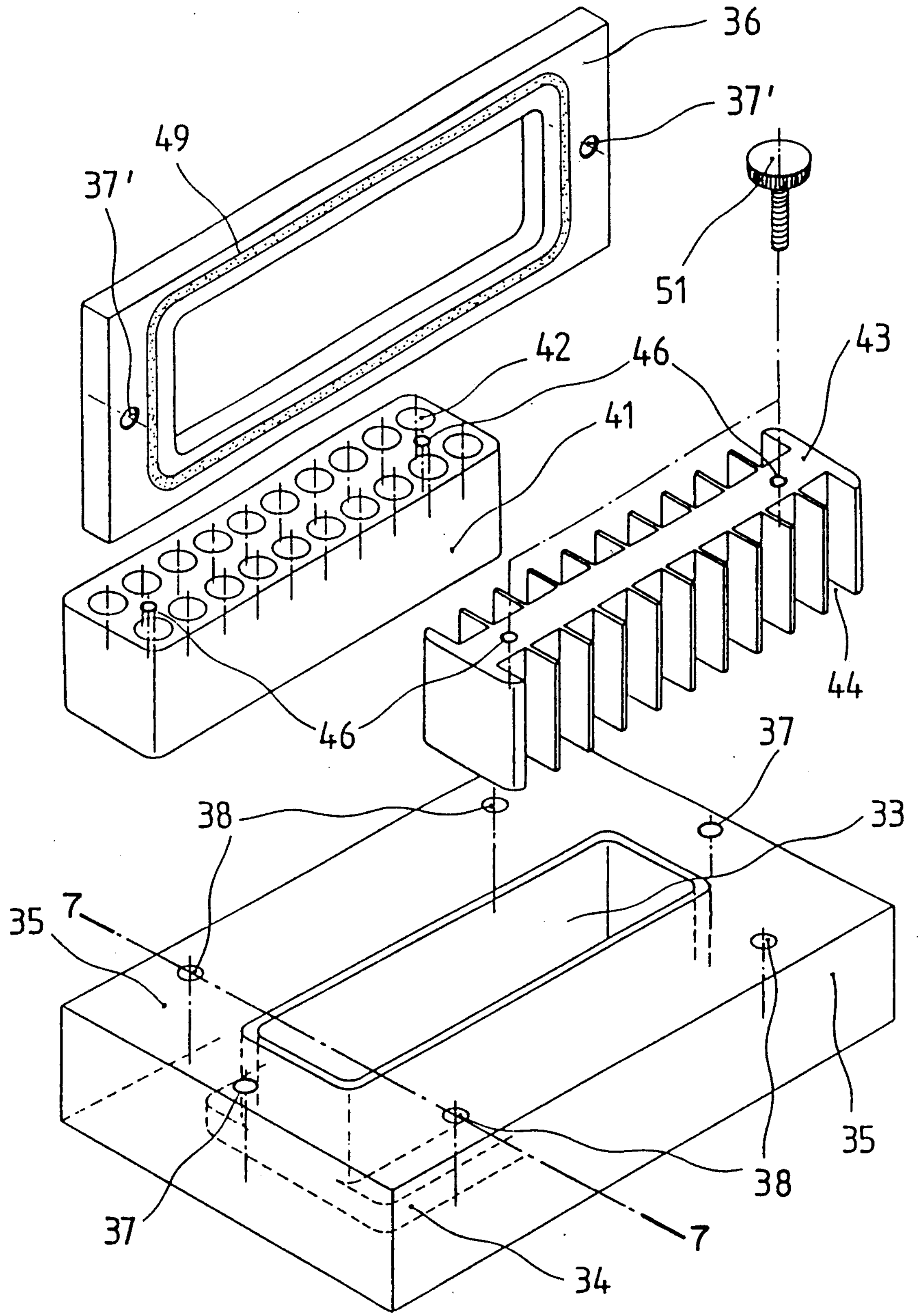
FIG. 6 is an exploded view showing a module with an open trough in perspective. The open trough (33) with the base plate (34) is enveloped by an insulating layer (35). The cover (36) with the gasket (49) can be screwed onto the working surface (2) of the metal block (1). The insert (41) serves for the use with tubes containing the samples, whereas the insert (43) with its square cells (44) is used to receive optical cuvettes with flat sides for spectroscopic work. The gripping screws (51) which are screwed into the holes (46) are used to manipulate the inserts (43) and (54).

In another form of the invention shown in FIGS. 6 and 7, the interchangeable module consists of an open trough (33) with a base plate (34), which partially extends beyond the sides of the trough, said base plate serving for the thermal contact with the working surface (2) of the metal block (1). The trough and the base plate may be made on one single piece of metal; the lower surface of the base plate has again to be exactly machined to ensure good thermal contact with the working surface (2). It can simply be put onto the working surface or be fixed by screws. All outer surfaces of the module, except the contacting face are thermally insulated. The top of the open trough is protected by an insulating cover, which, for better protection, can be provided with a sealing gasket (49). Moreover the insulating cover can be secured by screws.

The trough of the module can be filled with a liquid into which the sample vessels are immersed. A grid or a cover plate with openings may serve to keep the sample vessels in their position. Otherwise the trough can be filled with small particles of a heat-conducting solid, such as graphite or metal powder or spheres of metal or glass with a diameter not greater than about 5 millimeters. In such a filling the sample vessels can be stuck and held in their positions without any need for a further holding device. Moreover the interstices between the solid particles may be filled with a liquid, thus improving the heat transition to the sample vessels.

In still another form of the invention the open trough of the working module is provided with interchangeable inserts in the form of metal blocks with openings into which to introduce the sample vessels. Different inserts may be made available for different kinds of sample vessels, e.g. with round boreholes for tubes, or square cells for optical cuvettes with flat surfaces. The inserts have to be close-fitting in the trough, in order to ensure good heat transition. Means have therefore to be provided for inserting and extracting the inserts, e.g. in the form of gripping screws, which are screwed into corresponding holes of the insert. Very practically the same screws may be used for fixing the cover of the trough and, after removing the cover, for extracting the insert.

Figure 5A:
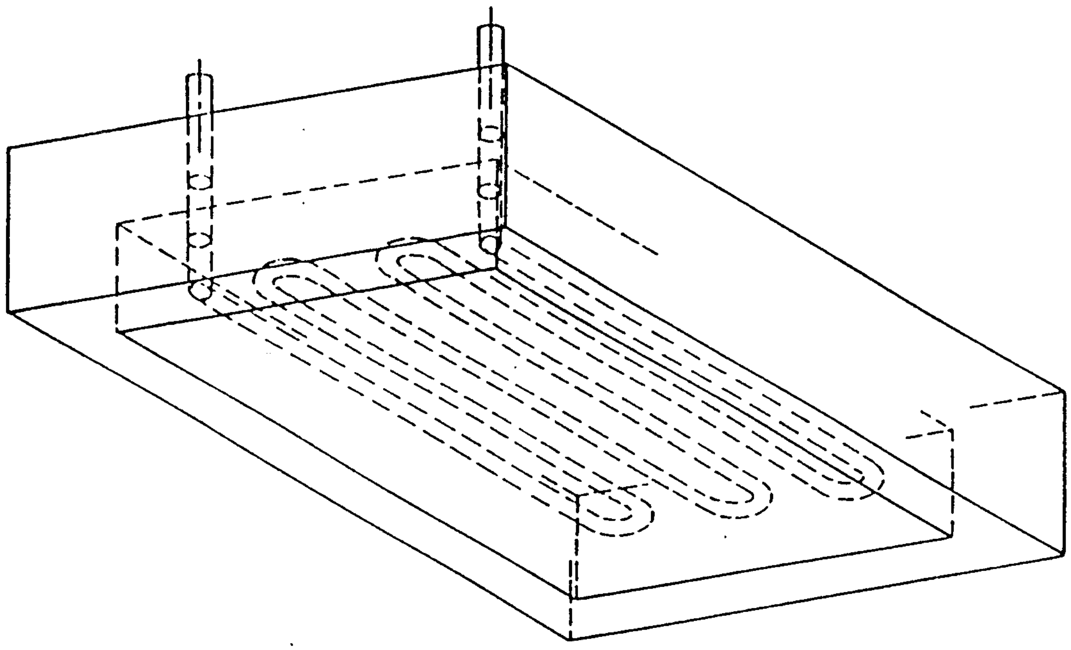
FIGS. 5*a* and 5*b* are perspective and end views, respectively, showing a module (17) with internal channels (18) through which a liquid to be cooled or heated can be pumped. The insulation envelope (19) is protecting the metal block of the module from any heat exchange with the environment.
Figure 5B:
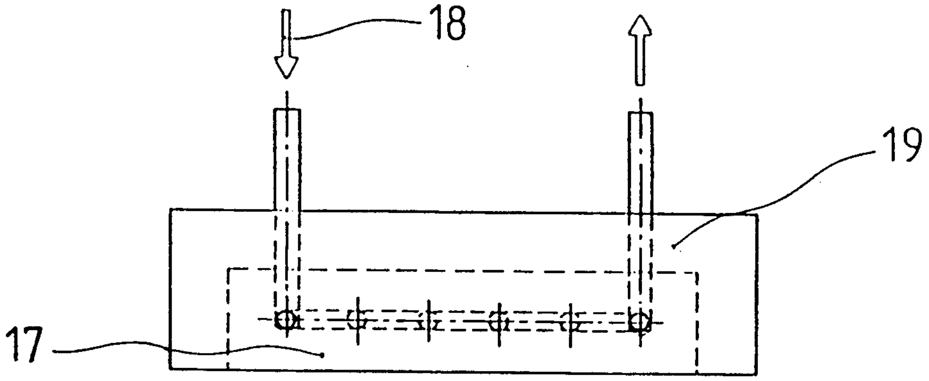

In another form of the invention shown in FIG. 5A and FIG. 5B, the working module (17) is provided with channels (18) in its interior, through which a liquid is circulated by a pump. This liquid can be the sample itself or a liquid such as water or alcohol for external heat exchange.

Figure 8:
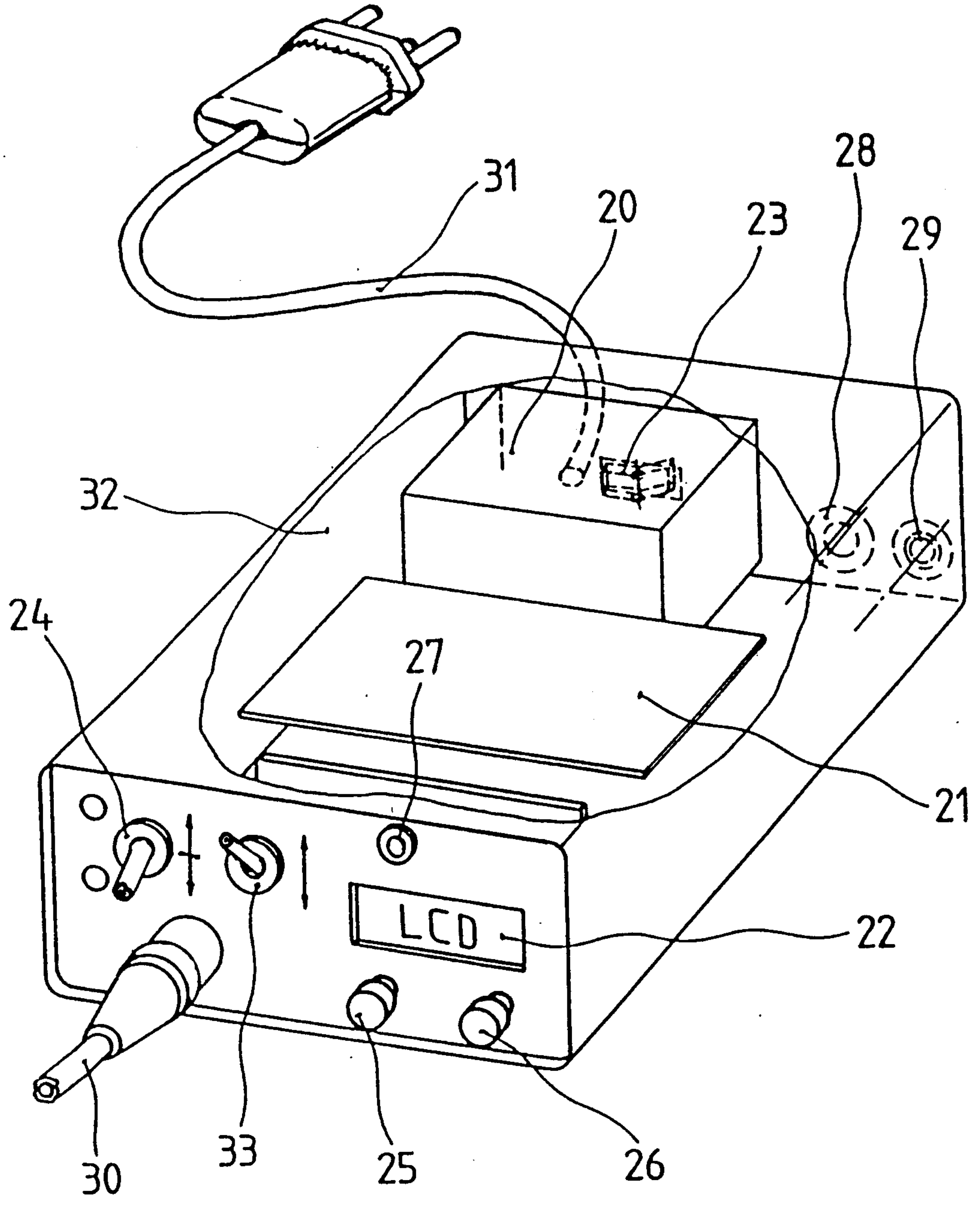
FIG. 8 is a perspective view of the alimentation and control unit (32) with the pulsed mains adaptor (20), the electronic control circuit (21), the LCD display (22) for the temperature, the mains switch (23), a switch (24) for selecting cooling or heating modes and a push-button switch for selecting indication of the preselected or the actual temperature. The temperature preselection is made by the push-button key (26).

As shown in FIG. 8, a power supply and control unit is provided for, with which the apparatus according to the invention is connected through the connection socket (27). This unit contains a transformer and rectifier (20) for generating the direct current needed for the alimentation of the Peltier elements on the one side and an electronic control circuit (21) to be influenced by a temperature sensor on the other side. By a microcomputer, which may be incorporated into the unit or externally connected to it by the socket (28), temperature cycles of any type may be programmed and executed.

Preferably the power supply for the Peltier elements is of the pulsed type: the alternating current of the mains is chopped with high frequency, subsequently transformed to low tension and finally rectified and smoothed for the alimentation of the Peltier elements (5). This type of alimentation allows to keep the volume and weight of the unit as small as possible and to minimize any energy loss by unwanted heat.

The control unit further contains a temperature indicating device (22) at which, according to choice, the preselected temperature of the actual temperature can be read. By means of the switch (33) either the temperature of the working surface (2) or of the sample can be displayed. The signals stem from the corresponding temperature sensors; one of them incorporated in the working block and another one (11) externally connected through the socket (27) for the temperature of the sample. The switch (24) of the control unit serves for interchanging cooling or heating modes of the working unit. When using a microcomputer for the programming of temperature cycles the function of switch (24) is taken over automatically by the control unit through comparison of the preselected and measured temperatures.

The alimentation of the apparatus is normally taken from the mains. It is however possible to feed the apparatus by direct current taken from an accumulator, e.g. an automobile battery of 12 V. It is therefore possible to use the apparatus in a mobile vehicle such as an automobile, the railroad or even in an airplane.

If the apparatus for heating and cooling is to be used under restricted space conditions or if the heat generated by the alimentation unit has to avoided in the surroundings of the sample, the separation of the working unit from the control and alimentation unit is of special advantage.

Referring to FIG. 8, (27) is a socket to connect the external temperature sensor; the connection for the temperature sensor (11) incorporated in the metal block (1) is comprised in the cable (30), which also contains the alimentation wires of the Peltier elements. For the alimentation the mains cable (31) or the socket (29) for a car battery may be used according to choice. The temperature indicator (22) can be switched between the internal or external sensors by the switch (33). An external microcomputer for programming temperatures cycles can be connected to the socket (28).

What is claimed is:

1. Laboratory apparatus for optionally heating or cooling samples, comprising a block of one or more Peltier elements which, with one of their thermal poles, are in thermal contact with an essentially rectangular block of heat conducting metal, and with the other pole are in thermal contact with a heat exchanger, the heat exchanger being thermally insulated from the metal block, one of the outer surfaces of the rectangular metal block being a substantially flat working surface for heating or cooling the samples, and all outer surfaces of the metal block, with the exception of the working surface and the surface in contact with the Peltier elements, being thermally insulated, whereby the working surface may be used for heating or cooling at will through inversion of the direction of the alimentation current for the Peltier elements.

2. Apparatus according to claim 1, characterized in that the heat conducting metal is aluminum or stainless steel.

3. Apparatus according to claim 1 characterized in that the heat exchanger is provided with channels through which a heat transporting liquid may be conducted.

4. Apparatus according to claim 1 characterized in that the heat exchanger is a metallic block provided with ribs, over which an air stream is blown by a ventilator.

5. Apparatus according to claim 1 comprising more than one Peltier element, characterized in that at least two out of the total number of Peltier elements are thermally arranged in series, said Peltier elements being arranged in a vertical stack with the opposite poles of two neighbouring elements in contact with one another.

6. Apparatus according to claim 1 characterized in that the current for the alimentation of the Peltier elements is governed by a control circuit comprising a temperature sensor.

7. Apparatus according to claim 1 characterized in that it comprises an exchangeable working module for holding vessels containing the samples to be heated or cooled, said working module comprising, on the one side, a face for contact with the flat working surface, and on the other side cavities for receiving the sample vessels.

8. Apparatus according to claim 7, characterized in that the working module is a rectangular block whose upper surface is provided with openings in which to receive the sample vessels and whose base serves as a contact surface to the working surface of the metal block, the remaining outer surfaces of the working module being thermally insulated.

9. Apparatus according to claim 7, characterized in that the working module comprises an open trough made of heat conducting metal which is provided with a base plate, which at least partially extends beyond the trough at its sides, the lower surface of this base plate serving for contact with the working surface of the metal block, the trough and the base plate, except its lower surface, being covered by an insulating layer.

10. Apparatus according to claim 9, characterized in that the trough of the working module is filled by a liquid and in that the trough includes a cover.

11. Apparatus according to claim 9, characterized in that the trough of the working module is filled by solid particles whose diameter does not exceed 5 millimeters, whereby the sample vessels may be positioned between the solid particles.

12. Apparatus according to claim 11, characterized in that the solid particles are spheres of metal or glass.

13. Apparatus according to claim 11, characterized in that the interstices between the solid particles are filled by liquid.

14. Apparatus according to claim 9, characterized in that the open trough is equipped with interchangeable inserts, which are provided with openings for receiving the vessels containing the samples.

15. Apparatus according to claim 1, further comprising a power supply for the Peltier elements, an electronic control circuit, a temperature indicating instrument and a commutator for choosing heating or cooling modes contained in a separate housing, this latter being connected by an electric cable to the Peltier elements, whereby a battery or a mains connection are used optionally for the electric alimentation.

16. Apparatus according to claim 15, characterized in that the control circuit is equipped with two temperature sensors, one of them measuring the temperature of the metal block in contact with the Peltier elements, and the other measuring the temperature of the sample, whereby, according to choice, any of the two sensors may be used separately, or both together to influence the control circuit.

17. Apparatus according to claim 15, comprising an alimentation and control unit provided with a microcomputer incorporated in, or externally connected thereto, this microcomputer being programmable for executing temperature cycles, whereby, if necessary, the temperatures in the cycle may be situated partly below and partly above ambient temperature and whereby, during the cycle, the apparatus is switched automatically from cooling to heating mode and vice-versa.

18. Apparatus according to claim 7, wherein the working module to be brought into contact with the metal block is equipped with interior channels for the transport of a liquid, whereby this liquid is either the sample itself or a heat transporting medium.

19. Apparatus according to claim 1, characterized in that a pulsed power supply is used for the alimentation of the Peltier elements.

* * * * *